US 9,750,465 B2

(12) United States Patent
Engel et al.

(10) Patent No.: US 9,750,465 B2
(45) Date of Patent: Sep. 5, 2017

(54) SCANNING SYSTEM FOR DIFFERENTIAL PHASE CONTRAST IMAGING

(75) Inventors: Klaus Juergen Engel, Aachen (DE); Dieter Geller, Aachen (DE); Gereon Vogtmeier, Aachen (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1218 days.

(21) Appl. No.: 13/514,312

(22) PCT Filed: Dec. 8, 2010

(86) PCT No.: PCT/IB2010/055662
§ 371 (c)(1),
(2), (4) Date: Jun. 7, 2012

(87) PCT Pub. No.: WO2011/070519
PCT Pub. Date: Jun. 16, 2011

(65) Prior Publication Data
US 2012/0236992 A1     Sep. 20, 2012

(30) Foreign Application Priority Data

Dec. 10, 2009  (EP) .................................... 09178696

(51) Int. Cl.
A61B 6/00     (2006.01)
A61B 6/03     (2006.01)

(52) U.S. Cl.
CPC .............. *A61B 6/00* (2013.01); *A61B 6/4291* (2013.01); *A61B 6/484* (2013.01); *A61B 6/488* (2013.01); *A61B 6/032* (2013.01); *A61B 6/5241* (2013.01)

(58) Field of Classification Search
CPC .... G21K 2207/005; A61B 6/00; A61B 6/032; A61B 6/484; A61B 6/488; A61B 6/4291
(Continued)

(56) References Cited

U.S. PATENT DOCUMENTS 4,242,583 A * 12/1980 Annis .................... G01N 23/04
378/146
5,319,693 A *  6/1994 Eberhard et al. ............... 378/19
(Continued)

FOREIGN PATENT DOCUMENTS

EP     0291299     11/1988
EP     1731099     12/2006
(Continued)

OTHER PUBLICATIONS

Reyes-Mena et al., Miniature x-ray tubes utilizing carbon-nanotube-based cold cathodes, 2005, Advances in X-ray Analysis, vol. 48, p. 204, 207.*

(Continued)

*Primary Examiner* — Glen Kao (57) ABSTRACT

The invention relates to the field of X-ray differential phase contrast imaging. For scanning large objects and for an improved contrast to noise ratio, an X-ray device (10) for imaging an object (18) is provided. The X-ray device (10) comprises an X-ray emitter arrangement (12) and an X-ray detector arrangement (14), wherein the X-ray emitter arrangement (14) is adapted to emit an X-ray beam (16) through the object (18) onto the X-ray detector arrangement (14). The X-ray beam (16) is at least partial spatial coherent and fan-shaped. The X-ray detector arrangement (14) comprises a phase grating (50) and an absorber grating (52). The X-ray detector arrangement (14) comprises an area detector (54) for detecting X-rays, wherein the X-ray device is adapted to generate image data from the detected X-rays and to extract phase information from the X-ray image data, the phase information relating to a phase shift of X-rays caused by the object (18). The object (18) has a region of interest (32) which is larger than a detection area of the X-ray detector (18) and the X-ray device (10) is adapted to (Continued)

generate image data of the region of interest (32) by moving the object (18) and the X-ray detector arrangement (14) relative to each other.

19 Claims, 6 Drawing Sheets

(58) Field of Classification Search
USPC .... 378/4, 8, 20, 62, 95, 125, 136, 205, 208, 378/209
See application file for complete search history.

(56) References Cited

U.S. PATENT DOCUMENTS

| | | | |
|---|---|---|---|
| 2004/0202280 A1* | 10/2004 | Besson | A61B 6/0414 378/37 |
| 2007/0183558 A1 | 8/2007 | Hempel | |
| 2007/0183583 A1 | 8/2007 | Baumann et al. | |
| 2009/0041189 A1* | 2/2009 | Allison | 378/95 |
| 2009/0168951 A1 | 7/2009 | Yan | |
| 2009/0238334 A1* | 9/2009 | Brahme et al. | 378/41 |
| 2009/0316857 A1* | 12/2009 | David | A61B 6/484 378/62 |
| 2010/0272235 A1 | 10/2010 | Takahashi | |

FOREIGN PATENT DOCUMENTS

| | | |
|---|---|---|
| EP | 1879020 | 1/2008 |
| JP | 2001043993 | 2/2001 |
| JP | 2005519668 | 3/2003 |
| JP | 2007203074 | 8/2007 |
| JP | 2007521911 | 8/2007 |
| JP | 2009165629 | 7/2009 |
| JP | 2009525115 | 7/2009 |
| WO | WO2009115966 | 9/2009 |

OTHER PUBLICATIONS

G.H. Chen et al., "Image Reconstruction for Fan-Beam Differential Phase contrast Computed Tomography", Physics in Medicine and Biology, vol. 53, No. 4, Feb. 21, 2008, pp. 1015-1025.

F. Pfeiffer et al., "Phase Retrieval and Differential Phase-Contrast Imaging With Low-Brilliance X-Ray Sources", vol. 2, Mar. 26, 2006, pp. 258-261.

Z. Huang et al., "X-Ray Phase Contrast Computed Tomographic Elementary Experiments Under Incoherent Conditions", Nuclear Science Symposium Conference Record, 2008, NSS '08, IEEE Oct. 19-25, 2008, pp. 593-596.

W. Ge et al., "An Outlook on X-Ray CT Research and Development", Medical Physics, AIP, vol. 35, No. 3, Feb. 25, 2008, pp. 1051-1064.

W.M. Atsushi, "Biomedical Imaging by Talbot-T X-Ray Phase Tomography", SPIE, vol. 6318, 2002.

Z. Qi et al., "An FBP Image Reconstruction Algorithm for X-Ray Differential Phase Contrast CT", SPIE, vol. 6913, 2008.

L. Zhang et al., "3D Reconstruction Algorithm for Cone-Beam Differential Phase Contrast Computed Tomography", Nuclear Science Symposium Conference Record, 2008, NSS 2008, IEEE Oct. 19-25, 2008, pp. 4193-4197.

* cited by examiner

SCANNING SYSTEM FOR DIFFERENTIAL PHASE CONTRAST IMAGING

FIELD OF THE INVENTION

The invention relates to the field of X-ray imaging. In particular, the invention relates to an X-ray device for imaging an object, a method for controlling an X-ray device, a computer-readable medium and a program element.

BACKGROUND OF THE INVENTION

X-ray differential phase-contrast imaging (DPCI) visualizes the phase information of coherent X-rays passing a scanned object. In addition to classical X-ray transmission imaging, DPCI may determine not only the absorption properties of the object along a projection line, but also the phase-shift of the transmitted X-rays, and thus may provide valuable additional information. After the object, a phase-shifting grating (also known as phase grating) is placed, working as a beam splitter. The resulting interference pattern contains the required information about the beam phase-shift in the relative position of its minima and maxima, typically in the order of several micrometers. Since a common X-ray detector, which may have a typical resolution in the order of 150 μm, may not be able to resolve such fine structures, the interference is sampled with a analyzer grating (also known as absorber grating), which features a periodic pattern of transmitting an absorbing strip with a periodicity similar to that of the interference pattern. The similar periodicity produces a Moiré pattern behind the grating with a much larger periodicity, which is detectable by a common X-ray detector. To obtain the differential phase-shift, the absorber grating and the phase grating are shifted laterally with respect to each other by fractions of the grating pitch, which is typically of the order of 1 μm. This movement is referred to as phase stepping or phase scanning. The phase-shift can be extracted from the particular Moiré pattern measured for each position of the absorber grating.

For example, in EP 1 731 099 A1, an X-ray interferometer arrangement is shown that can be used to execute grating-based differential phase-contrast imaging. The X-ray interferometer comprises an incoherent X-ray source with a source grating and a detector arrangement with a phase grating and an absorber grating.

SUMMARY OF THE INVENTION

In grating-based differential phase-contrast imaging, gratings with high aspect ratio are used. These gratings may need to be aligned well with the optical axis of the system. From a practical and of manufacturing point of view, the trenches or lamellae of the gratings may have to be preferable orthogonal to a flat substrate. If such a flat grating/detector arrangement is used, the visibility of structures of the object may drop quickly with the distance of the object to the optical axis. In particular, if the distance orthogonal to the grating orientation is considered, the visibility may drop quickly due to the misalignment between the trenches of the gratings and the X-rays. In the direction parallel to the orientation of the gratings, due to the increasing distance to the X-ray source, also the visibility may decrease.

For an effective use, the grating lamellae may need to be aligned almost parallel to the incident X-ray wave vector. Otherwise, intended rectangular profiles for X-ray absorption or X-ray phase-shift become trapezoidal distant from the optical center, which may result in a strong decrease in the visibility of interference pattern and therefore in a degradation of the contrast to noise ratio.

A further problem may arise from incoherently scattered X-ray radiation, which may be scattered by the object. The additionally scattered photons may create an unwished signal offset in the absorption image and may decrease the contrast to noise ratio not only in absorption image but also in the differential phase-contrast image.

There may be a need for an X-ray device for differential phase contrast imaging provided to scan large objects and having an improved contrast to noise ratio.

This need may be met by the subject-matter of the independent claims. Exemplary embodiments of the invention are evident from the dependent claims.

A first aspect of the invention relates to an X-ray device for imaging an object.

According to an embodiment of the invention, the X-ray device comprises an X-ray emitter arrangement and an X-ray detector arrangement, wherein the X-ray emitter arrangement is adapted to emit an X-ray beam through the object onto the X-ray detector arrangement. The X-ray emitter arrangement may be a device on one side of the object and the X-ray detector arrangement may be a further device on another side of the object, for example opposite to the X-ray emitter arrangement. For example for medical applications, the object may be a human or an animal lying on a table and the X-ray emitter arrangement is located over the object and the X-ray detector arrangement is located below the object on the table.

According to an embodiment of the invention, the X-ray emitter arrangement is adapted to generate an X-ray beam that is at least partial spatial coherent. It has to be understood, that an at least partial spatial coherent X-ray beam may comprise X-rays that are only locally spatial coherent. For example, only X-rays that are separated from each other less than 1 μm may have to be coherent.

According to an embodiment of the invention, the X-ray emitter arrangement may comprise an X-ray source for generating spatial incoherent X-rays, for example an X-ray tube, and a source grating for creating an at least partial spatial coherent X-ray beam from the incoherent X-rays from the X-ray source. With such an arrangement, a beam of at least partial spatial coherent X-rays may be formed.

According to an embodiment of the invention, the X-ray emitter arrangement is adapted to generate a fan-shaped X-ray beam.

A fan-shaped X-ray beam may be a beam substantially in the form of a cone, i.e. the X-rays of the beam are coming from a region that is very small with respect to the object of interest, wherein the dimensions of the cone orthogonal to the axis of the cone substantially differ from each other. These two dimensions may be defined by a fan angle and a cone angle of the beam, wherein the fan angle is the small angle and the cone angle is the large angle, which may be as large that the fan-shaped beam covers the whole region of interest of the object.

Also, a fan-shaped beam may be a beam in the form of a pie slice, wherein thickness or width of the pie slice is small compared to the length of the pie slice. In this case, the X-rays are parallel with respect to the thickness direction and spread with respect to another direction.

A first dimension of the fan-shaped beam may be much larger than a second dimension, when the first dimension of the beam is at least 5 to 10 times longer than the second dimension of the beam. For example, the fan-shaped beam may have a rectangular cross-section orthogonal to the optical axis of the system wherein the one side of the rectangle is at least 5 to 10 times longer than the other side of the rectangle.

According to an embodiment of the invention, the X-ray emitter arrangement comprises a collimator for limiting the X-ray beam to a fan-shaped X-ray beam. For example, the X-ray emitter arrangement may comprise an X-ray source that generates a coherent X-ray beam and the collimator generates a fan-shaped coherent X-ray beam from the X-rays emitted from the X-ray source.

For example, the X-ray emitter arrangement may be equipped with a collimator generating a fan-beam and a source grating which generates a number of X-ray lines near the X-ray focal spot. The size of the detector along the axial direction may be limited to a range within which no significant degradation effects due to misaligned grating lamellae or slits may be expected.

According to an embodiment of the invention, the X-ray detector arrangement comprises a phase grating and an absorber grating. A grating may be a plurality of parallel aligned slits or trenches, wherein the grating is more transparent to X-rays at the slits or trenches as between them. For example, the slits or trenches may be formed by lamellae that are formed on a substrate.

According to an embodiment of the invention, the X-ray device is adapted to move the phase grating and the absorber grating relative to each other, in particular for executing a phase scanning step. For example, the X-ray device may comprise a step motor or piezo actuator for moving the phase grating with respect to the absorber grating or vice versa. By moving the two gratings relative to each other, behind the grating interference patterns are created that may be used to extract information, how the phase of spatial coherent X-rays has been shifted by the object. Generally, the X-ray device may be adapted to move the phase grating, the absorber grating and/or the source grating for executing a phase scanning step.

According to an embodiment of the invention, the X-ray detector arrangement may comprise a detector for detecting X-rays. With such a detector, the interference patterns created by the phase grating and the absorber grating may be analyzed. For example, such a detector may comprise detector elements that are adapted to detect the intensity of X-rays falling on the respective detector element, i.e. the detector may be a detector for detecting intensities of X-rays. As a second example, the X-ray detector may be a detector adapted for counting photons, i.e. the detection of X-rays may be executed by counting X-ray photons falling onto the detector.

According to an embodiment of the invention, the X-ray detector is an area detector. An area detector may be a detector that is adapted to detect a two-dimensional image. For example, an area detector may comprise detector elements or pixels that are arranged at a face of the detector in two dimensions for example in a rectangular pattern. It may be possible that the detection area of the detector does not have to be planar.

According to an embodiment of the invention, the area detector, the phase grating and/or the absorber grating are adapted to the fan-shaped X-ray beam. This may mean that the area detector, the phase grating and the absorber grating may substantially have the same shape as the fan-shaped X-ray beam at the respective position of the respective component of the X-ray detector arrangement (i.e. the phase grating, the absorber grating and/or the area detector). For example, if the X-ray beam has a rectangular cross-section, the phase grating, the absorber grating and/or the X-ray detector may have a rectangular form. The phase grating, the absorber grating and the X-ray detector may have the same dimensions as the fan-shaped X-ray beam. For example, if the distance between the X-ray source or the X-ray emitter arrangement and the detector or the X-ray detector arrangement is about 1 m, the width of the detector in the direction orthogonal the fan-shaped beam may be about 6 cm. However, the (maximal) width of the detector may be smaller or larger. The width of the detector may be dependent on the aspect ratio, i.e. the relationship between height and pitch, of the used grating.

For example, to scan the field of view of a region of interest of the object, a detector with a small fan angle, but a large cone angle that covers the entire object may be used. At each detector position, several projections may be taken with different relative grating positions, i.e. a phase scanning is performed, in order to allow phase retrieval.

According to an embodiment of the invention, the X-ray device is adapted to generate image data from the detected X-rays and to extract phase information from the X-ray image data wherein the phase information relates to a phase-shift of X-rays caused by the object. As already said, by moving the phase grating and the absorber grating relative to each other, interference patterns from the X-rays transmitted through the object are created on the area detector. At a number of relative positions of the phase grating and the absorber gratings image data may be taken with the detector. From these image data, which contain interference patterns in the form of differing X-ray intensities, the phase-shift from one point to another point may be determined.

According to a further embodiment of the invention, the object has a region of interest which is larger than a detection area of the X-ray detector. The X-ray device may be adapted to generate image data of the region of interest by moving the object and the X-ray detector arrangement relative to each other.

In other words, the X-ray device may adapted to move the object and the X-ray detector arrangement relative to each other, such that a region of interest of the object may be scanned that is larger than the X-ray detector arrangement.

This may have the advantage that the X-ray device has a high visibility in all parts of the scanned image and an improve contrast to noise ratio.

For example, in a first step at a first relative position of the object and the X-ray detector, a phase scanning of a first part of the region of interest of the object may be done. I.e. at the first relative position, a series or plurality of raw data images with different relative positions of the phase grating and the absorber grating are recorded. With this series of raw data images, the X-ray device may create first image data, representing phase information of the first part of the region of interest. After that, in a second step, the X-ray device may move the object and the X-ray detector arrangement into a second relative position different from the first relative position. At this second relative position, the X-ray device scans a second part of the region of interest of the object. This is again done by taking a series of raw data images at different relative positions of the phase grating and the absorber grating. From these series or plurality of raw data images, the X-ray device may create second image data containing phase information of the second part of the region of interest.

After that, the X-ray device may add the second image data to the first image data, to create aggregated image data containing phase information of the first part of the region of interest and of the second part of the region of interest.

In other words, the X-ray device may be adapted to aggregate first image data containing phase information of a first part of the region of interest with second image data containing phase information of a second part of the region of interest to aggregated image data. The single image data may be put together to aggregated image data.

It has to be understood that the above-mentioned steps may be repeated, i.e. a third part of the region of interest may be scanned and so on. The steps may be repeated until the whole region of interest is scanned.

According to an embodiment of the invention, the X-ray emitter arrangement comprises an X-ray source with X-ray emitter lines adapted to generate the fan-shaped spatial at least partial coherent X-ray beam. In other words, the X-ray emitter arrangement may comprise a structured X-ray source comprising emitter lines, wherein the emitter lines fulfil substantially the same functions as the slits of the source grating. However, the emitter lines themselves may generate the X-rays.

According to an embodiment of the invention, the X-ray emitter lines comprise a cathode with carbon nanotubes or other distributed X-ray sources for emitting electrons. Such an arrangement may have the advantage, that carbon nanotubes may be adapted to emit electrons at room temperature.

According to an embodiment of the invention, the grating lines or grating slits of the source grating, the phase grating and/or the absorber grating are aligned parallel to the fan-shaped X-ray beam. The gratings may be aligned with the long edge of the detector.

According to an embodiment of the invention, the X-ray device is adapted to move the object and the X-ray detector arrangement relative to each other in an axial direction orthogonal to the fan-shaped X-ray beam. Further, the X-ray device may be adapted to move the object and the X-ray detector arrangement together with the X-ray emitter arrangement relative to each other in the axial direction. In other words, the X-ray detector arrangement and the X-ray emitter arrangement may be rigidly mechanically connected with each other.

The X-ray device may be adapted to conduct the movement in steps. Further each step may be adapted to the width or thickness of the detector, such that the image data taken at the different relative positions may be easily aggregated. It may also be possible, that the steps are such that the image data slightly overlap.

According to an embodiment of the invention, the X-ray device comprises an actuator for moving the object with respect to the X-ray emitter arrangement and the X-ray detector arrangement. The X-ray emitter arrangement and the X-ray detector arrangement may be stationary with respect to the vicinity of the X-ray device or with respect to the ground and with respect to each other.

The object may be attached to a component of the X-ray device movable by the X-ray device, for example the object is a human being lying on a movable table, wherein the X-ray device is able to move the component into the axial direction in defined steps, while differential phase contrast imaging snapshots or image data of object slices are performed at each scan position. This may have the advantage that the field of view is not limited in the axial direction except for the possible limits of the X-ray device, which can be extended very easily. A further advantage may be that no cone beam has to be used, i.e. a beam with a large fan angle and thus the incoherently scattered X-ray radiation may be limited to arise only in that volume of the object which is illuminated by the fan-beam, which may be quite smaller than the volume which would be illuminated for a large field of view detector.

According to an embodiment of the invention, the X-ray device may comprise an actuator for moving the X-ray emitter arrangement and/or the X-ray detector arrangement with respect to the object. In this case, the object may be stationary with respect to the vicinity of the X-ray device.

For example, the object may be fixed stationary, while the X-ray emitter arrangement and the X-ray detector arrangement which may be connected with each other may be moved in defined steps or continuously with respect to the object.

According to an embodiment of the invention, the X-ray device comprises an actuator for moving the X-ray emitter arrangement and/or the X-ray detector arrangement around the object, for example in a rotational movement. In this case, the X-ray detector arrangement may be moved around the object to different positions, for example with the help of a rail the detector arrangement is sliding on, and the X-ray emitter arrangement may be rotated around an axis, such that the emitted fan-shaped X-ray beam falls onto the detector. However, it is possible, that the X-ray emitter arrangement and the X-ray detector arrangement are rigidly mechanically connected, for example by a arm, and are rotated around a common rotation axis.

A large field of view may be covered by rotating the detector arrangement around an axis through the focal spot.

The X-ray device performing a rotational motion of the detector and/or the X-ray emitter arrangement may be used for mammography.

The relative movement of the object and the X-ray detector arrangement (may be together with the X-ray emitter arrangement) either linear or rotational may comprise a plurality of steps. In each step, image data, which has a small dimension with respect to the moving direction due to the fan-shaped beam, but which may comprise the whole region of interest in the direction orthogonal to the movement, may be recorded. After that, the image data may be joined to a complete image of this complete region of interest of the object.

According to an embodiment of the invention, the X-ray device is adapted to move at least one grating, for example the phase grating, the absorber grating or the source grating (for example in the axial direction) such that the one grating remains fixed with respect to the object, when the object moves relative to the X-ray emitter arrangement or the X-ray detector arrangement. In other words, at least one of the gratings is moved such that in the moving reference system of the object a phase scanning of the object may be executed.

In this case, the grating lines may be aligned orthogonal to the scan axis or axial direction. Therefore, the phase stepping direction may be parallel to the axial direction (linear relative movement) or substantially parallel to the rotation direction (rotational movement of the object).

In this case, the movement of at least one grating may be performed in large steps, wherein the relative movement of the object and the detector arrangement may be performed in small steps or continuously. The movement of the at least one grating in a large step may be executed between two phase stepping sequences.

For example, the phase stepping may be performed in large steps for the source grating (for example by a scanning actuator means) and in smaller steps (or continuously) for either the object or the detector arrangement. Generally, it is also possible that the large steps may be also performed for the phase grating and/or the absorber grating.

For example, a large step may be identical to n small steps with n being the number of total phase steps per view or per phase scanning.

This arrangement may have the advantage, that larger masses (for example the object or the whole X-ray device except the source grating) have not to be accelerated during single steps, but can be instead moved in a constant speed.

An efficient way to combine the scanning direction with the direct direction of phase stepping may be possible if the grating lines are aligned orthogonal to the axial direction. In this case, one of the gratings may be kept at a fixed position during a phase stepping cycle or phase stepping step, while the other gratings (in general combined with the X-ray emitter and/or detector arrangement as an inertial mass) may be moved with constant speed. After a phase scanning cycle or a phase scanning step, the fixed grating (with low mass) can be moved in a large step by a slice width.

According to an embodiment of the invention, the X-ray emitter arrangement comprises an X-ray source with switchable emitter lines. This means, that not all the emitter lines may be activated together but that some or all of the emitter lines may be switched on and off independently from each other. For example, this may be done with an anode above a cathode with carbon nanotubes, wherein the anode comprises different strips they may be independently from each other connected with a voltage source.

According to an embodiment of the invention, the X-ray emitter arrangement is larger in the direction of movement than the X-ray detector arrangement, wherein the X-ray device is adapted to switch the emitter lines such that solely the emitter lines opposite to the X-ray detector arrangement are switched on for a phase scan. For example, the X-ray source may be spatially fixed but may provide individually switchable emitter lines over the whole scanning range. While the detector may be moved continuously or in steps, the emitter lines currently opposite of the detector arrangement may be individually switched on and off.

If the extension of an X-ray emitter arrangement is made large enough with individually switchable emitter lines, it may be possible that the stepping of the X-ray emitter arrangement becomes obsolete, as single emitter lines may be switched on or off directly opposite to the moving X-ray detector arrangement.

According to an embodiment of the invention, the X-ray device is adapted to analyze an X-ray intensity of the X-rays at the X-ray detector arrangement during a first scan step. For example, the detected X-ray intensity is analyzed by the X-ray device during the scan for each position in order to evaluate the dose efficiency.

According to an embodiment of the invention, the X-ray device is adapted to set an intensity of the X-rays emitted by the X-ray emitter arrangement for a second scan step based on the analyzed X-ray intensity of the first scan step. For example, the X-ray intensity for each line or for each scan position is adapted for dose efficiency using the dose efficiency analysis results of prior scanned lines or positions.

According to an embodiment of the invention, the X-ray device is adapted to set the scan speed of a second scan step based on the analyzed X-ray intensity of the first scan step. The scan speed during a scan step may be the speed of the movement of the object or the X-ray emitter arrangement or the X-ray detector arrangement. The scan speed may also be the speed of the grating during one phase scanning step. For example, the scan speed and thus the X-ray exposure per line or per scan step is adapted for dose efficiency using the dose efficiency analysis results of prior scanned lines or prior scan steps.

The first scan step and the second scan step may be individually phase scanning steps at different relative positions of the components of the X-ray device, when the X-ray device is moving the object and the X-ray detector arrangement relative to each other continuously or in small steps.

For example, the image data of a line or the image data generated during one phase scanning step may be real-time analyzed for dose efficiency, in order to maintain a homogeneous contrast to noise ratio. As a result of the dose efficiency analysis, either the X-ray intensity or the scan speed may be adjusted or set. Also a combination thereof may be adjusted or set. For example, in a medical imaging application only a thin object slice may be scanned for a phase scanning step and the dose spent for the next step and therefore the total harmfulness to the patient due to X-ray exposure may be reduced.

This may have the advantage that the X-ray dose a patient is exposed may be decreased. If a large detector is used, a local illuminating X-ray intensity is directly coupled to the tube load, which means that the dose which may be optimally adapted to a first part of the image area might not be optimally adapted to another area of the image area, which, for example, may be caused by different object thicknesses at the two areas. The applied X-ray intensity is adapted to the local object properties during the overall scan, in order to optimize the deposited dose for a more homogeneous contrast to noise ratio in the image.

A further aspect of the invention is a method for controlling an X-ray device.

According to an embodiment of the invention, the method comprises the steps of: generating a fan-shaped at least partial spatial coherent X-ray beam; transmitting the X-ray beam through an object, a phase grating and an absorber grating onto an X-ray area detector; generating image data from X-rays detected by the X-ray area detector; extracting phase information from the image data, the phase information relating to a phase-shift of X-ray caused by the object.

According to an embodiment of the invention, the method comprises the steps of: moving the object and the X-ray detector arrangement relative to each other; generating image data of a region of interest of the object, wherein the region of interest is larger than a detection area of the X-ray area detector.

According to an embodiment of the invention, the method comprises the step of: Generating the fan-shaped at least partial spatial coherent X-ray beam with an X-ray source having X-ray emitter lines, in particular X-ray emitter lines comprising a cathode with carbon nanotubes.

According to an embodiment of the invention, the method comprises the step of: Moving at least one grating, for example the phase grating, the absorber grating or the source grating such that the at least one grating remains fixed with respect to the object, when the object, the X-ray emitter arrangement and/or the X-ray detector arrangement move relative to each other.

According to an embodiment of the invention, the method comprises the steps of:

Moving the object, the X-ray emitter arrangement and/or the X-ray detector continuously or in small steps relative to each other; Moving at least one of the gratings in large steps.

According to an embodiment of the invention, the method comprises the step of:

Analyzing an X-ray intensity of the X-rays at the X-ray detector arrangement during a first scan step.

According to an embodiment of the invention, the method comprises the step of:

Setting an intensity of the X-rays emitted by the X-ray emitter arrangement for a second scan step based on the analyzed X-ray intensity of the first scan step.

According to an embodiment of the invention, the method comprises the step of:

Setting a scan speed of a second scan step based on the analyzed X-ray intensity of the first scan step.

It has to be understood that method steps described with respect to the device may also be embodiments of the method and vice versa.

The X-ray device and the method for controlling an X-ray device may be used in stationary transmission geometries (i.e. mammography, fluoroscopy) but also for computed tomography (CT) or related rotational X-ray imaging technologies.

A further aspect of the invention relates to a computer-readable medium, in which a computer program for controlling an X-ray device is stored, which, when being executed by a processor (for example a processor of the X-ray device), is adapted to carry out the steps of the method as described in the above and in the following.

A computer-readable medium may be a floppy disk, a hard disk, an USB (Universal Serial Bus) storage device, a RAM (Random Access Memory), a ROM (Read Only memory) and an EPROM (Erasable Programmable Read Only Memory). A computer readable medium may also be a data communication network, e.g. the Internet, which allows downloading a program code.

A further aspect of the invention relates to a program element (for example a computer program) for controlling an X-ray device, which, when being executed by a processor (for example a processor of the X-ray device), is adapted to carry out the steps of the method as described in the above and in the following.

These and other aspects of the invention will be apparent from and elucidated with reference to the embodiment described hereinafter.

BRIEF DESCRIPTION OF THE DRAWINGS

Below, embodiments of the present invention are described in more detail with reference to the attached drawings.

The reference symbols used in the drawings, and their meanings, are listed in summary form in the list of reference symbols. In principle, identical parts are provided with the same reference symbols in the figures.

DETAILED DESCRIPTION OF EMBODIMENTS

Figure 1:
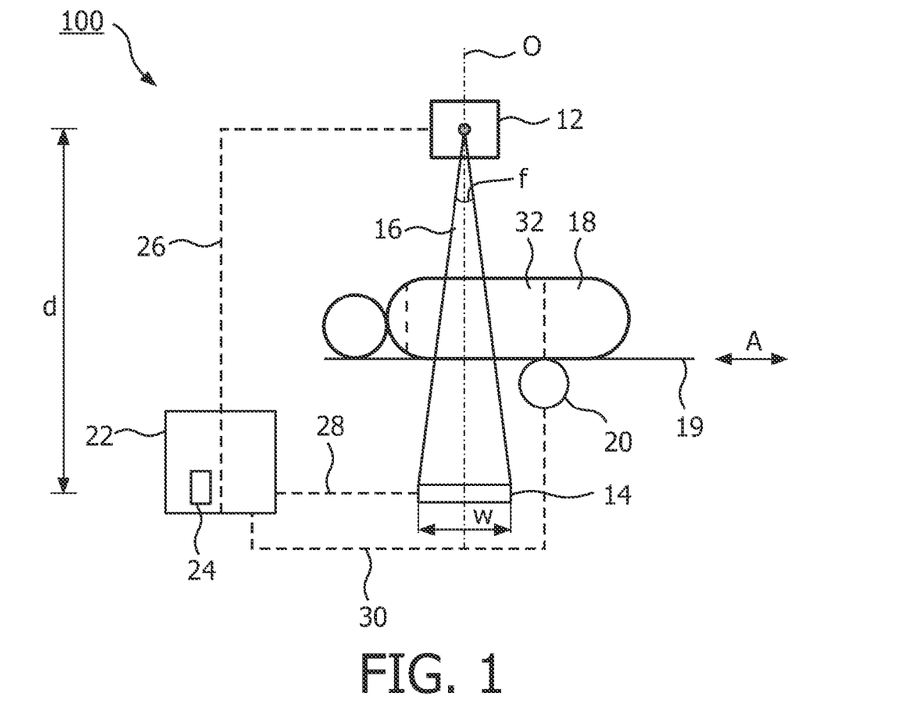
FIG. 1 shows an X-ray device according to an exemplary embodiment of the invention.

FIG. 1 shows schematically an X-ray device 10 with an X-ray emitter arrangement 12 and an X-ray detector arrangement 14. The X-ray emitter arrangement 12 is adapted to emit a fan-shaped and at least partial coherent X-ray beam 16. The X-ray beam 16 is transmitted through an object 18 for example a human being, on a table 19.

In the embodiment shown in FIG. 1, the X-ray emitter arrangement 12 and the X-ray detector arrangement 14 are stationary with respect to the environment of the X-ray device 10 and the object 18 may be moved in an axial direction A orthogonal to the optical axis O of the X-ray device 10. For moving the table 19 in the axial direction A, the X-ray device 10 comprises an actuator 20, for example step motor 20, that is adapted to move the table 19 with the object 18 in small steps in the axial direction A.

The X-ray device 10 further has a controller 22 with a processor 24. The controller 22 is connected to the X-ray emitter arrangement 12 over a signal line 26, to the X-ray detector arrangement 14 over a signal line 28 and to the actuator 20 over a signal line 30. Over these signal lines 26, 28, 30, the controller 22 controls the X-ray emitter arrangement 12, the X-ray detector arrangement 14 and the actuator 20. Further, the controller 22 is adapted to receive image data taken by the X-ray detector arrangement 14 over the signal line 28.

As shown in FIG. 1, the fan-shaped beam 16 has a small fan angle f and the detector 14 has a width w that is adapted to this small fan angle f. For example, if the distance d between the X-ray emitter arrangement 12 and the X-ray detector arrangement 14 is about 1 m, the width w of the detector arrangement 14 may be 6 cm, or even smaller. This may guarantee a good visibility even at the ends of the detector arrangement 14 in the direction A.

Since the fan angle f of the beam 16 is small, not the entire region of interest 32 of the object 18 is covered by the X-ray beam 16.

Figure 2:
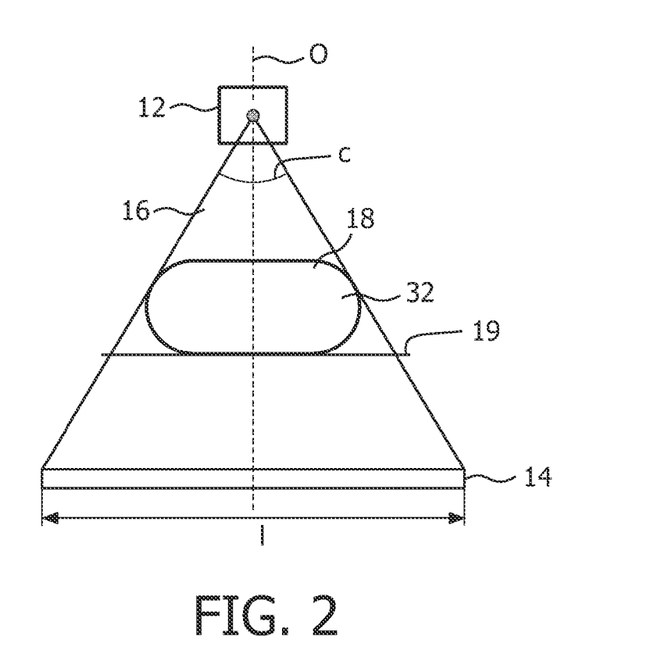
FIG. 2 shows an X-ray device according to an exemplary embodiment of the invention in a different direction.

FIG. 2 shows an X-ray emitter arrangement 12 and an X-ray detector arrangement 14 that may be used together with all the embodiments of X-ray devices shown in the figures.

FIG. 2 shows a view of the X-ray beam 16 in the direction A of FIG. 1. The X-ray beam 16 has a cone angle c that is much larger than the fan angle f. Also, the detector arrangement 14 has a length l that is much larger than the width w of the X-ray detector arrangement 14. For example, the length l may be about 50 cm. Due to the large cone angle c of the beam 16, the entire object 18 or the entire region of interest 32 is covered by the fan-shaped beam 16 in a plane orthogonal to the axial direction A.

Figure 3:
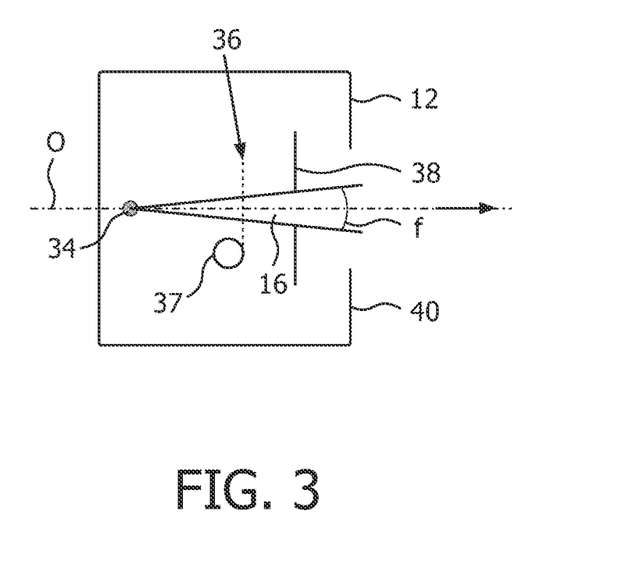
FIG. 3 shows an X-ray emitter arrangement according to an exemplary embodiment of the invention.

FIG. 3 shows an embodiment of an X-ray emitter arrangement 12. The X-ray emitter arrangement 12 comprises an incoherent X-ray source 34, for example an X-ray tube 34, a source grating 36 and a collimator 38. All these components 34, 36, 38 may be situated inside a housing 40 of the X-ray detector arrangement 12. The X-ray source 34 may be activated and deactivated by the controller 22 over the signal line 26. When the X-ray source 34 is working, it emits incoherent X-ray beams, which fall on the source grating 36. After leaving the source grating 36, the X-ray beam 16 is locally coherent. With the collimator 38 the X-ray beam 16 is limited to a small fan angle f and to the cone angle c.

The X-ray emitter arrangement 12 may further comprise an actuator 37 for moving the source grating 36 (for example a piezo drive or step motor 37).

Figure 4:
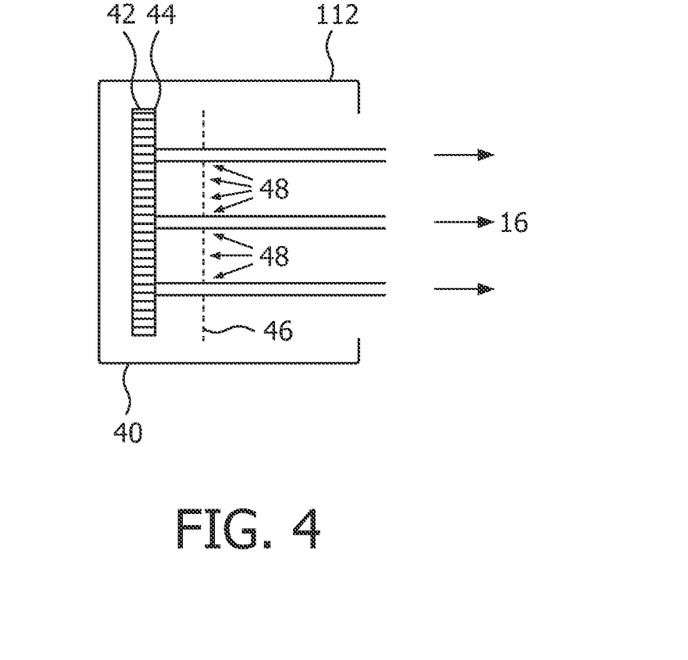
FIG. 4 shows an X-ray emitter arrangement according to an exemplary embodiment of the invention.

FIG. 4 shows a further embodiment of an X-ray emitter arrangement 112. The X-ray emitter arrangement 112 comprises a cathode 42 with carbon nanotube based emitters (or other cold cathode emitters) 44 and an anode 46. The anode 46 comprises several elements they may be connected to a voltage source or high voltage generator independently from each other by the controller 22 Alternatively, the single carbon nanotube emitters 44 may be switched independently from each other and the anode 46 has a connection to a high voltage generator. As indicated in FIG. 4, only certain anode elements are radiating and X-rays are produced only at the (activated) anode elements.

The X-ray emitter arrangement 112 has therefore several emitter lines 48 that may be activated independent from each other by the controller 22.

It has to be noted, that the X-ray beam 16 produced by the X-ray emitter arrangement 112 has parallel X-rays. However, by using a bent anode 42, a X-ray beam 16 as shown in FIG. 6, which has X-rays that are spreading in two directions or an X-ray beam with X-rays that are only spreading in one direction, for example as for the X-ray device of FIG. 9, may be produced.

Figure 5:
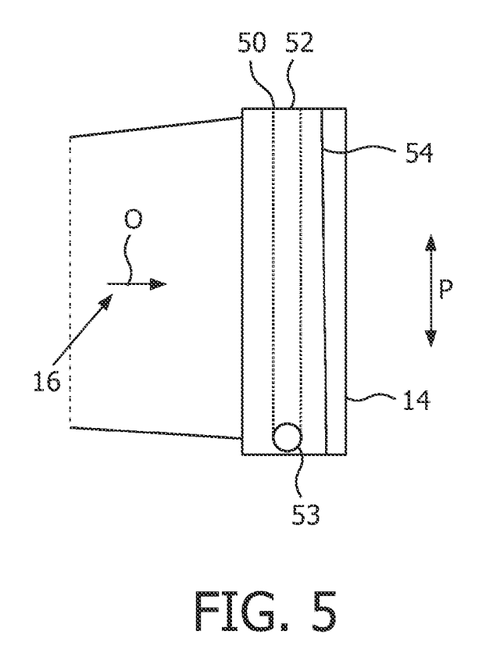
FIG. 5 shows an X-ray detector arrangement according to an exemplary embodiment of the invention.

FIG. 5 shows a X-ray detector arrangement 14 with phase grating 50, absorber grating 52 and an area detector 54. The components 50, 52, 54 of the X-ray detector arrangement 14 all may be situated in a housing 56. The X-ray detector arrangement 14 comprises an actuator 53 for moving the phase grating 50 and absorber grating 52 relative to each other in the direction P.

For conducting a complete phase scan, the controller 22 may move the phase grating 50 and the absorber grating 52 relative to each other in the direction P (which may be parallel to the direction A) in small steps. Due to the X-rays 16 which have passed the object 18 and are falling onto the phase grating 50 and the absorber grating 52, patterns of different intensity of X-rays are formed on the area detector 54. At each of the plurality of relative positions of the phase grating 50 and the absorber grating 52, the detector 54 takes an image of the respective intensities and sends this raw image data to the controller 22. From the plurality of different raw image data taken during one phase scan, the controller 22 calculates image data containing phase information of the X-rays passed through the object 18.

Figure 6:
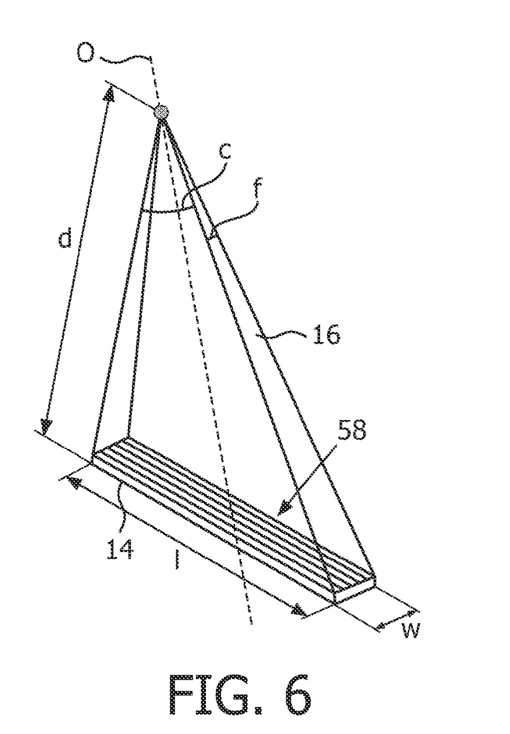
FIG. 6 shows a three-dimensional view of an X-ray beam and a detector according to an exemplary embodiment of the invention.

FIG. 6 shows a three-dimensional view of the cone-beam 16 and the X-ray detector arrangement 14. As may be seen from FIG. 6, the grating lines 58 of the phase grating 50 and the absorber grating 52 are parallel to the longer sides of the X-ray detector arrangement 14. In other words, the grating lines 58 may be orthogonal to the axial direction A.

The X-ray device shown in FIG. 1 may be controlled by the controller 22 in the following way:

The object 18 is moved by the table 19 (and the actuator 20) to a position wherein a first slice of the region of interest 32 may be imaged. At this position a first phase stepping, i.e. scanning of the part of the region of interest 32 is conducted and the respective image data is produced. After that, the object 18 is moved to the next position wherein the next slice of the region of interest 32 is scanned. Also, image data of this second slice is produced by the controller 22.

The distance between the two positions is such that the image data obtained at the two positions slightly overlap, such that aggregated image data may be obtained.

In this way, the X-ray device 10 takes image data from further slices of the region of interest 32 until the whole region of interest 32 is scanned. The entire image data taken at the different positions of the object containing phase information of the different slices of the region of interest 32 may at the end be aggregated to one image containing information on the whole region of interest 32.

Besides the movement of the object 18 in large steps, it is also possible in an alternative embodiment to move the object 18 in very small steps or continuously.

During the continuous movement of the object 18, the whole region of interest 32 is scanned and the phase scanning is combined with the movement of the object 18. To this end, at least one of the gratings 36, 50, 52 has to be kept at a fixed position with respect to the object 18 during a phase stepping cycle. After a phase scanning cycle, the fixed grating(s) 36, 50, 52 has to be moved in a large step by a slice. At each phase scanning cycle, image data from the respective slices of the region of interest 32 are taken, which at the end can be put together or aggregated to aggregated image data showing the whole region of interest 32.

Figure 7:
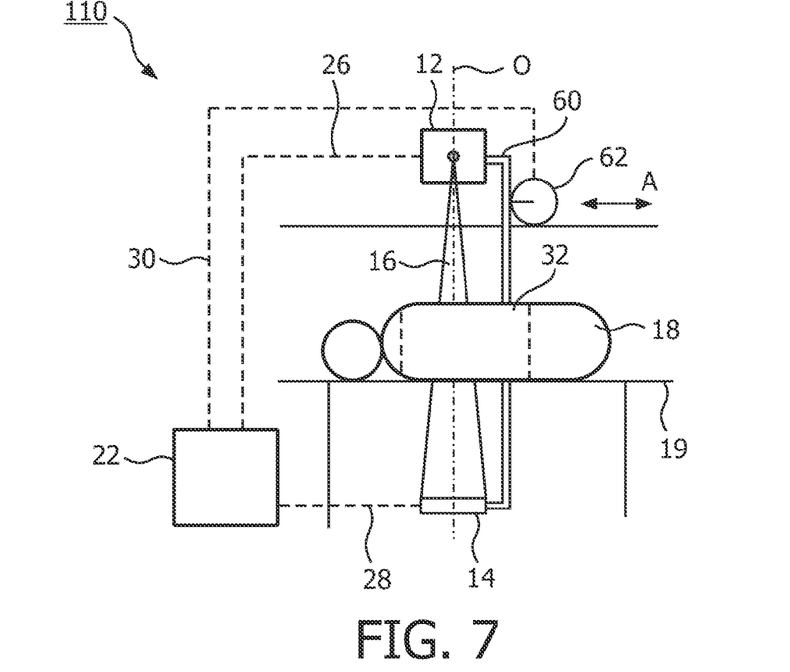
FIG. 7 shows an X-ray device according to an exemplary embodiment of the invention.

FIG. 7 shows a further embodiment of an X-ray device 110. Contrary to the X-ray device 10 of FIG. 1, the X-ray device 110 has a stationary table 19. Thus the object 18 remains stationary with respect to environment of the X-ray device 110. The X-ray emitter arrangement 12 and the X-ray detector arrangement 14 of the X-ray device 110 are rigidly connected with each other, for example by an arm 60, with which both the arrangements 12 and 14 may be moved in the axial direction A with the aid of an actuator 62.

Similar to the embodiment of FIG. 1, the movement of the combination of the X-ray emitter 12 and the X-ray detector 14 can be executed either in steps or continuously. If the movement is conducted in steps, at each step, the X-ray device 110 may take image data of the region of interest 32 and at the end may aggregate an overall image of the region of interest 32. If the movement is done continuously or in small steps, the phase scanning and the movement have to be combined as described above with respect to the embodiment of FIG. 1.

Figure 8:
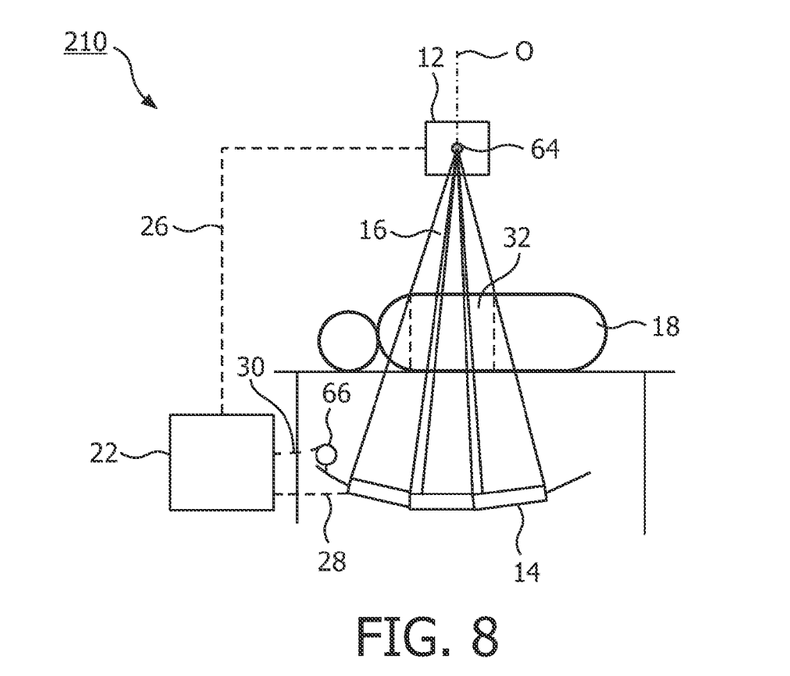
FIG. 8 shows an X-ray device according to a further exemplary embodiment of the invention.

FIG. 8 shows a further embodiment of an X-ray device 210. In the embodiment shown in FIG. 8, the X-ray device 210 is adapted to rotate the X-ray detector arrangement 14 about the focal spot 64 of the X-ray device 210. FIG. 8 shows the detector arrangement 14 in three different positions, in which the X-ray beams 16 directed to the X-ray detector arrangement 14 covers the whole region of interest 32.

For the movement of the X-ray detector arrangement 14, the X-ray device 210 comprises an actuator 66. Further, the X-ray emitter arrangement 12 is rotatable about the focal spot 64. For example, the X-ray emitter arrangement 12 and the X-ray detector arrangement 14 are connected with each other by an arm, which may be rotated around an axis. Contrary as indicated in FIG. 8, this rotation also may be around an axis that is different from an axis through the focal spot 64.

As already explained with respect to the X-ray devices 10 and 110 of FIG. 1 and FIG. 7, respectively, the rotational movement of the X-ray detector arrangement 14 may either be conducted in large steps or continuously (or in small steps), wherein in the first case, phase scanning is executed at each position and in the second case the phase scanning is combined with the continuous movement of the detector arrangement 14 with respect to the object 18.

Figure 9:
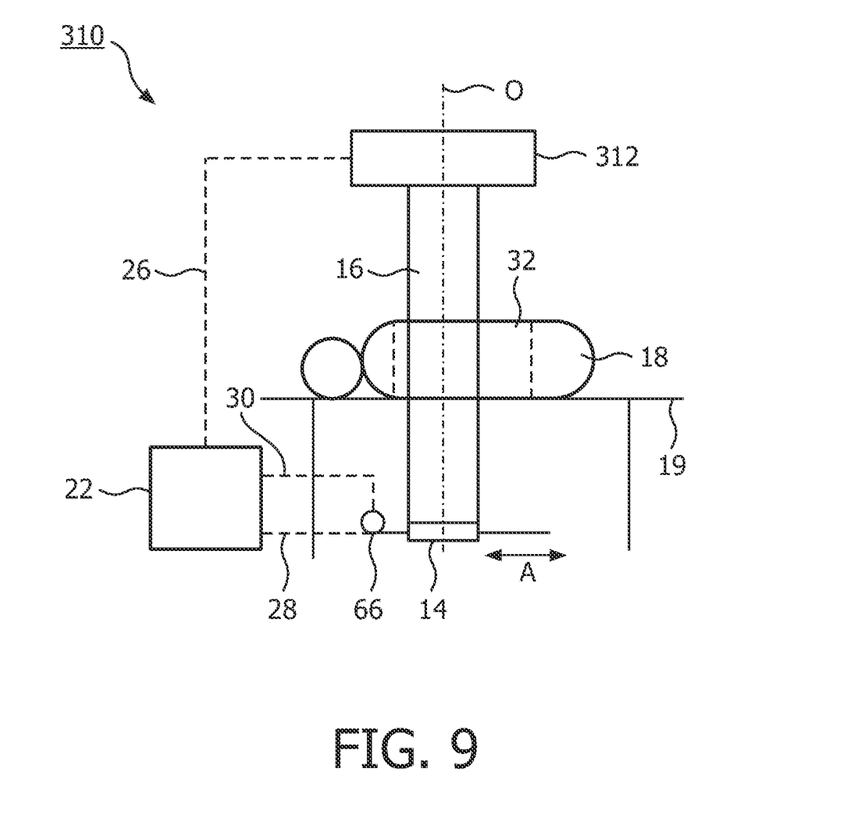
FIG. 9 shows an X-ray device according to a further exemplary embodiment of the invention.

FIG. 9 shows a further embodiment of an X-ray device 310. The X-ray device 310 comprises an X-ray emitter arrangement 312 wherein the X-ray emitter arrangement 312 comprises an X-ray emitter that is adapted to generate an emitter beam 16 within the whole scanning region. For example, the X-ray emitter arrangement 312 may be designed like the X-ray emitter arrangement 112 shown in FIG. 4 with a plurality of emitter lines distributed over the extension of the X-ray emitter arrangement 312 in the direction A.

The X-ray emitter device 310 comprises an X-ray detector arrangement 14 that is movable along the direction A, for example by an actuator 66 like a step motor or piezo drive 66. When the X-ray detector arrangement 14 is moved to a certain position, only the emitter lines 48 opposite to the X-ray emitter arrangement 14 may be activated to generate the X-ray beam 16.

Again the movement of the X-ray detector arrangement may be conducted in large steps or continuously, wherein either at each position a phase scan is conducted or the phase scanning is combined with the continuous movement.

Figure 10:
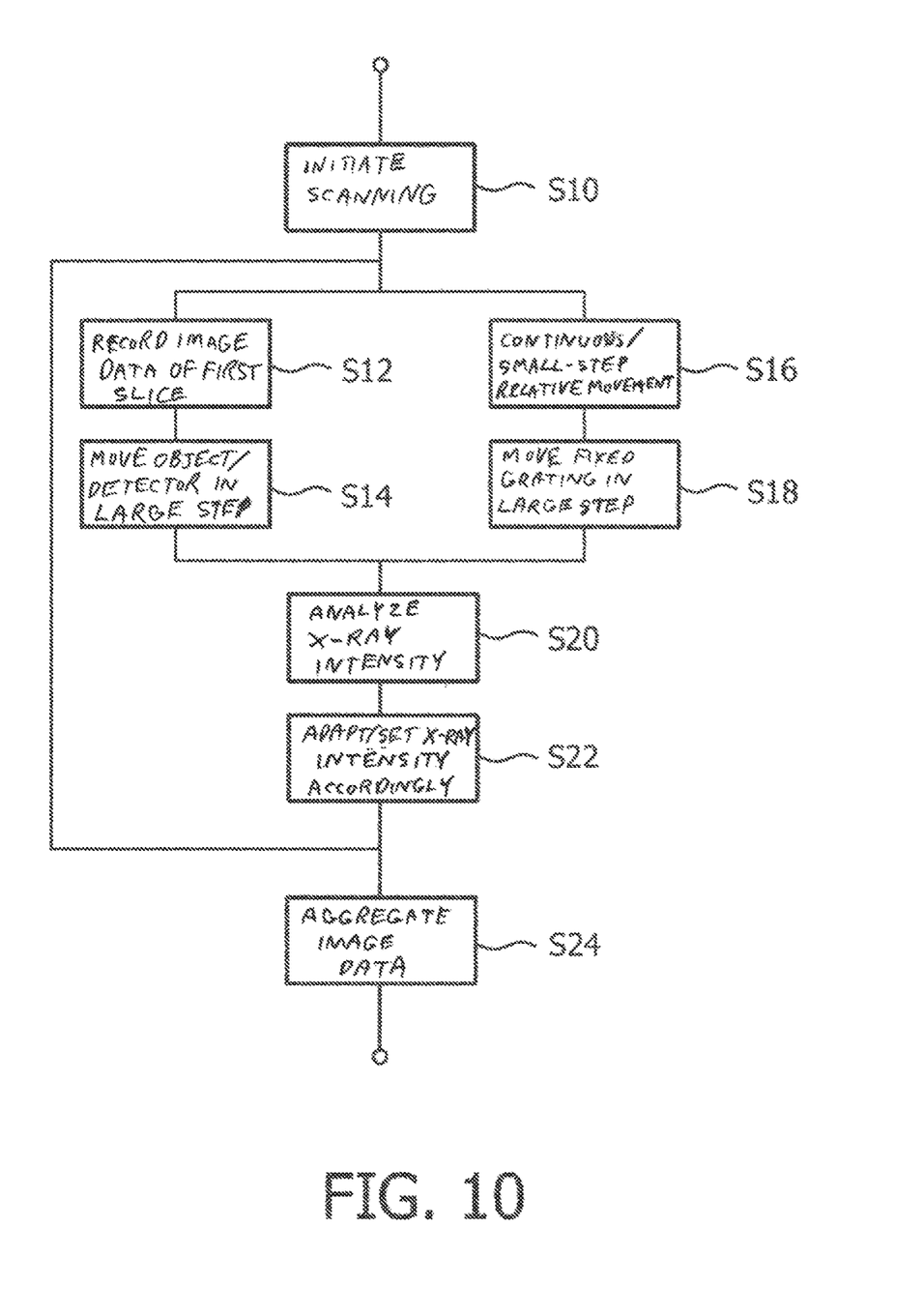
FIG. 10 shows a flow diagram for a method for controlling an X-ray device according to an exemplary embodiment of the invention.

FIG. 10 shows a flow diagram of a method of controlling an X-ray device 10, 110, 210, 310 that may be executed by the processor 24 of the controller 22.

In a step S10, the scanning of the region of interest 32 is initiated by moving either the object 18 or the detector arrangement 14 to the start position, where the scanning has to be started.

In a step S12, image data of a first slice of the region of interest 32 is recorded. After that, in step S14, either the object 18 or the X-ray detector arrangement 14 are moved in a large step to the next relative position were the next phase scanning has to be made.

Alternatively, the phase scanning of a slice of the region of interest 32 may be done while the object 18 or the X-ray detector arrangement 14 is moving continuously or in small steps. To this end, in step S16, a continuous movement or a movement in small steps of the object 18 and the X-ray detector arrangement 14 relative to each other is started during which the phase scanning is performed. After that, in a step S18, the fixed grating, 36, 50, 52 has to be moved in a large step by a slice width.

In both cases, in a step S20, the X-ray intensity is analyzed by analyzing the recorded image data to evaluate the dose efficiency of the actual scan.

In a step S22, the X-ray intensity of the X-ray emitter arrangement 12, 112, 312 may be adapted or set, using the dose efficiency analysis results of step S20. Alternatively or additionally, the scan speed, i.e. the speed of the movement of the gratings 36, 50, 52 and/or the speed of the movement of the object 18 relative to the arrangements 12, 14, is adapted or set, using the dose efficiency analysis results of step S20.

After that, if not the end of the region of interest 32 has been reached, the method continues either at step S12 or at step S16 for executing a phase scan for the next slice.

If the whole region of interest 32 has been scanned, in step S24, the image data scanned for the different slices covering the region of interest 32 are aggregated or put together to form an overall image data containing a scan of the whole region of interest 32.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SIGNS 10, 110, 210, 310 X-ray device
12, 112 X-ray emitter arrangement
14 X-ray detector arrangement
16 X-ray beam
18 object
O optical axis
A axial direction
19 table
20 actuator
22 controller
24 processor
26, 28, 30 signal line
32 region of interest
f fan angle of beam
c cone angle of beam
w width of detector
d distance of emitter arrangement to detector arrangement
l length of detector
34 X-ray source
36 source grating
37 actuator
38 collimator
40 housing
42 cathode
44 carbon nanotube emitters
46 anode
48 emitter lines
50 phase grating
52 absorber grating
53 actuator
54 area detector
56 housing
P direction of movement of gratings
58 grating lines
60 arm
62 actuator
64 focal spot
66 actuator

The invention claimed is:
1. An X-ray device for imaging an object, comprising:
an X-ray emitter arrangement, and
an X-ray detector arrangement,
wherein the X-ray emitter arrangement is adapted to emit an X-ray beam through the object onto the X-ray detector arrangement,
wherein the X-ray beam is spatially at least partially coherent,
wherein the X-ray beam is fan-shaped,
wherein the X-ray detector arrangement comprises a phase grating and an absorber grating,
wherein the X-ray detector arrangement comprises a detector for detecting X-rays,
wherein the X-ray detector is an area detector,
wherein the X-ray device is adapted to generate image data from the detected X-rays and to extract phase information from the X-ray image data, the phase information relating to a phase shift of X-rays caused by the object, wherein the object has a region of interest which is larger than a detection area of the X-ray detector and the X-ray device is adapted to generate image data of the region of interest by moving the object and the X-ray detector arrangement relative to each other, wherein the X-ray emitter arrangement comprises an X-ray source with switchable emitter lines, wherein the X-ray emitter arrangement, in a direction of relative movement, of the X-ray detector arrangement with respect to the X-ray emitter arrangement, that is orthogonal to the beam, is larger than the X-ray detector arrangement, wherein the X-ray device is adapted to switch the emitter lines such that solely the emitter lines opposite to the X-ray detector arrangement are switched on.

2. The X-ray device of claim 1, wherein the X-ray emitter lines are adapted to generate said X-ray beam, wherein the X-ray emitter lines comprises a cathode with carbon nanotubes.

3. The X-ray device of claim 1, further comprising:
an actuator for moving the object with respect to the x-ray emitter arrangement and the x-ray detector arrangement;
an actuator for moving the X-ray detector arrangement with respect to the object;
an actuator for moving at least one of the X-ray emitter arrangement and the X-ray detector arrangement around the object; or
any combination of the actuators.

4. The X-ray device of claim 1, wherein the X-ray device is adapted to move at least one of the phase grating, the absorber grating and a source grating such that the at least one grating remains fixed with respect to the object, when relative movement among any of the object, the X-ray emitter arrangement and the X-ray detector arrangement occurs.

5. The X-ray device of claim 1, wherein the X-ray device is adapted to analyze an X-ray intensity of the X-rays at the X-ray detector arrangement during a first scan step.

6. The X-ray device of claim 5, wherein the X-ray device is adapted to set an intensity of the X-rays emitted by the X-ray emitter arrangement for a second scan step based on the analyzed X-ray intensity of the first scan step.

7. The X-ray device of claim 5, wherein the X-ray device is adapted to set a scan speed of a second scan step based on the analyzed X-ray intensity of the first scan step.

8. An X-ray device for imaging an object, comprising:
an X-ray emitter arrangement, and
an X-ray detector arrangement,
wherein the X-ray emitter arrangement is adapted to emit an X-ray beam through the object onto the X-ray detector arrangement,
wherein the X-ray beam is spatially at least partially coherent,
wherein the X-ray beam is fan-shaped,
wherein the X-ray detector arrangement comprises a phase grating and an absorber grating,
wherein the X-ray detector arrangement comprises a detector for detecting X-rays,
wherein the X-ray detector is an area detector,
wherein the X-ray device is adapted to generate image data from the detected X-rays and to extract phase information from the X-ray image data, the phase information relating to a phase shift of X-rays caused by the object, wherein the object has a region of interest which is larger than a detection area of the X-ray detector and the X-ray device is adapted to generate image data of the region of interest by moving the object and the X-ray detector arrangement relative to each other, wherein said device has a focal spot, and wherein the movement-based generating entails rotating said X-ray detector arrangement around an axis that goes through said focal spot while said focal spot remains stationary.

9. The X-ray device of claim 8, said rotating being performed to cover a larger field of view than obtained without said rotating.

10. The X-ray device of claim 8, wherein said object includes a person having a torso that has a longitudinal direction, said beam passing through said torso at an angle transverse to said longitudinal direction.

11. The X-ray device of claim 8, wherein the beam is cone-shaped with two dimensions of the cone orthogonal to an axis of the cone being equal or differing.

12. A non-transitory computer-readable medium embodying a computer program for controlling an X-ray device, said program having instructions executable by a processor for performing a plurality of acts, from among said plurality there being the acts of:
generating a fan-shaped X-ray beam that is spatially at least partially coherent,
transmitting the X-ray beam through an object, a phase grating and an absorber grating onto an X-ray area detector,
generating image data from X-rays detected by the X-ray area detector,
extracting phase information from the image data, the phase information relating to a phase shift of X-rays caused by the object;
moving, relative to each other, the object and an X-ray detector arrangement comprising said X-ray area detector; and
generating image data of a region of interest of the object, wherein the region of interest is larger than a detection area of the X-ray area detector, wherein said X-ray beam has a focal spot and among said plurality there further being the act of rotating said X-ray detector arrangement around an axis that goes through said focal spot while said focal spot remains stationary.

13. The computer readable medium of claim 12, wherein said object includes a person having a torso that has a longitudinal direction, said beam passing through said torso at an angle transverse to said longitudinal direction.

14. The computer readable medium of claim 12, wherein said generating is such that said beam is cone-shaped with two dimensions of the cone orthogonal to an axis of the cone being equal or differing.

15. A non-transitory computer readable medium embodying a computer program for controlling an X-ray device, said program having instructions executable by a processor for performing a plurality of acts, from among said plurality there being the acts of:
emitting, via an X-ray emitter arrangement, an X-ray beam through the object onto an X-ray detector arrangement, wherein the X-ray beam is spatially at least partially coherent, wherein the X-ray beam is fan-shaped, wherein the X-ray detector arrangement comprises a phase grating and an absorber grating, wherein the X-ray detector arrangement comprises a detector for detecting X-rays, wherein the X-ray detector is an area detector;

generating, via said X-ray device, image data from the detected X-rays;

extracting phase information from the X-ray image data, the phase information relating to a phase shift of X-rays caused by the object, wherein the object has a region of interest which is larger than a detection area of the X-ray detector;

generating image data of the region of interest by moving the object and the X-ray detector arrangement relative to each other, wherein the X-ray emitter arrangement comprises an X-ray source with switchable emitter lines, wherein the X-ray emitter arrangement, in a direction of relative movement, of the X-ray detector arrangement with respect to the X-ray emitter arrangement, that is orthogonal to the beam, is larger than the X-ray detector arrangement; and switching the emitter lines such that solely the emitter lines opposite to the X-ray detector arrangement are switched on.

16. The computer readable medium of claim 15, wherein the X-ray device is adapted to move at least one of the phase grating, the absorber grating and a source grating such that the at least one grating remains fixed with respect to the object, when relative movement among any of the object, the X-ray emitter arrangement and the X-ray detector arrangement occurs.

17. The computer readable medium of claim 15, wherein the X-ray device is adapted to analyze an X-ray intensity of the X-rays at the X-ray detector arrangement during a first scan step.

18. The computer readable medium of claim 17, wherein the X-ray device is adapted to set an intensity of the X-rays emitted by the X-ray emitter arrangement for a second scan step based on the analyzed X-ray intensity of the first scan step.

19. The computer readable medium of claim 17, wherein the X-ray device is adapted to set a scan speed of a second scan step based on the analyzed X-ray intensity of the first scan step.

* * * * *